United States Patent [19]

Sakagami

[11] Patent Number: 4,785,407

[45] Date of Patent: Nov. 15, 1988

[54] AUTOMATIC CHEMICAL ANALYZER WITH SELECTIVE REMOVAL OF REACTION VESSELS

[75] Inventor: Toshio Sakagami, Cofu, Japan

[73] Assignee: Olympus Optical Co., Ltd., Tokyo, Japan

[21] Appl. No.: 928,459

[22] Filed: Nov. 10, 1986

[30] Foreign Application Priority Data

Nov. 19, 1985 [JP] Japan .................. 60-257542

[51] Int. Cl.$^4$ .................. G01N 31/00; G01N 35/06
[52] U.S. Cl. .................. 364/497; 364/500; 356/246; 422/64; 422/67
[58] Field of Search .......... 364/496, 497, 499, 500, 364/502, 413, 507; 356/244, 246, 414, 416; 422/62–64, 67, 100

[56] References Cited

U.S. PATENT DOCUMENTS

| | | | |
|---|---|---|---|
| 4,158,545 | 6/1979 | Yamashita et al. | 364/497 |
| 4,366,119 | 12/1982 | Takeuchi | 364/497 |
| 4,406,547 | 9/1983 | Aihara | 356/414 |
| 4,422,151 | 12/1983 | Gilson | 364/496 |
| 4,457,893 | 7/1984 | Takekawa | 364/497 |
| 4,459,265 | 7/1984 | Berglund | 364/497 |

FOREIGN PATENT DOCUMENTS 2610808 2/1978 Fed. Rep. of Germany.
3133191 1/1982 Fed. Rep. of Germany.

Primary Examiner—Parshotam S. Lall
Assistant Examiner—Brian M. Mattson
Attorney, Agent, or Firm—Parkhurst, Oliff & Berridge

[57] ABSTRACT

An automatic chemical analyzer including a cuvette wheel having a number of cuvette holding recesses formed along a periphery thereof, a driving unit for rotating the cuvette wheel in a stepwise manner, an automatic cuvette loader for supplying cuvettes into cuvette holding recesses of the cuvette wheel, a sample delivery device for supplying samples into cuvettes held on the cuvette wheel, a reagent delivery device for supplying reagents into cuvettes held on the cuvette wheel, a colorimeter for measuring an optical density of test liquids contained in cuvettes, a washing device for washing cuvettes, and an automatic cuvette unloader for removing cuvettes out of the cuvette wheel. The analyzer further comprises a central control device for controlling the automatic cuvette loader and unloader such that after a cuvette has been repeatedly used a predetermined maximum number of times, the relevant cuvette is removed from the cuvette wheel and a new cuvette is supplied into the cuvette holding recess from which the cuvette has been just removed.

4 Claims, 7 Drawing Sheets

FIG_1

FIG_3

FIG_5
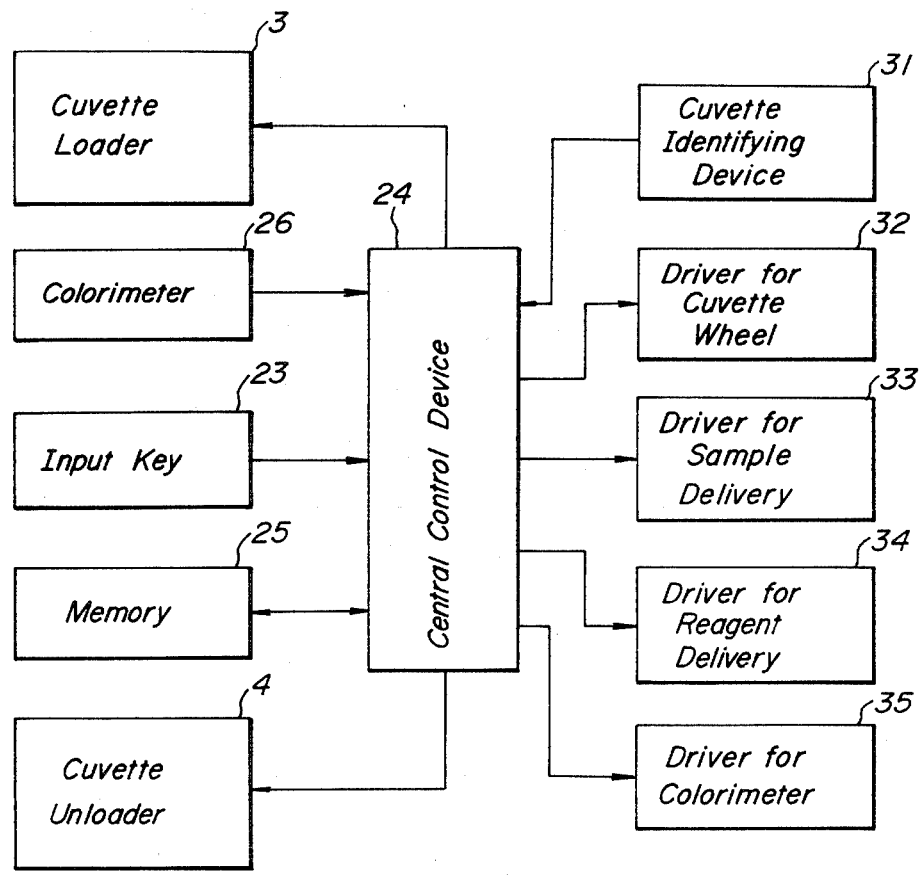

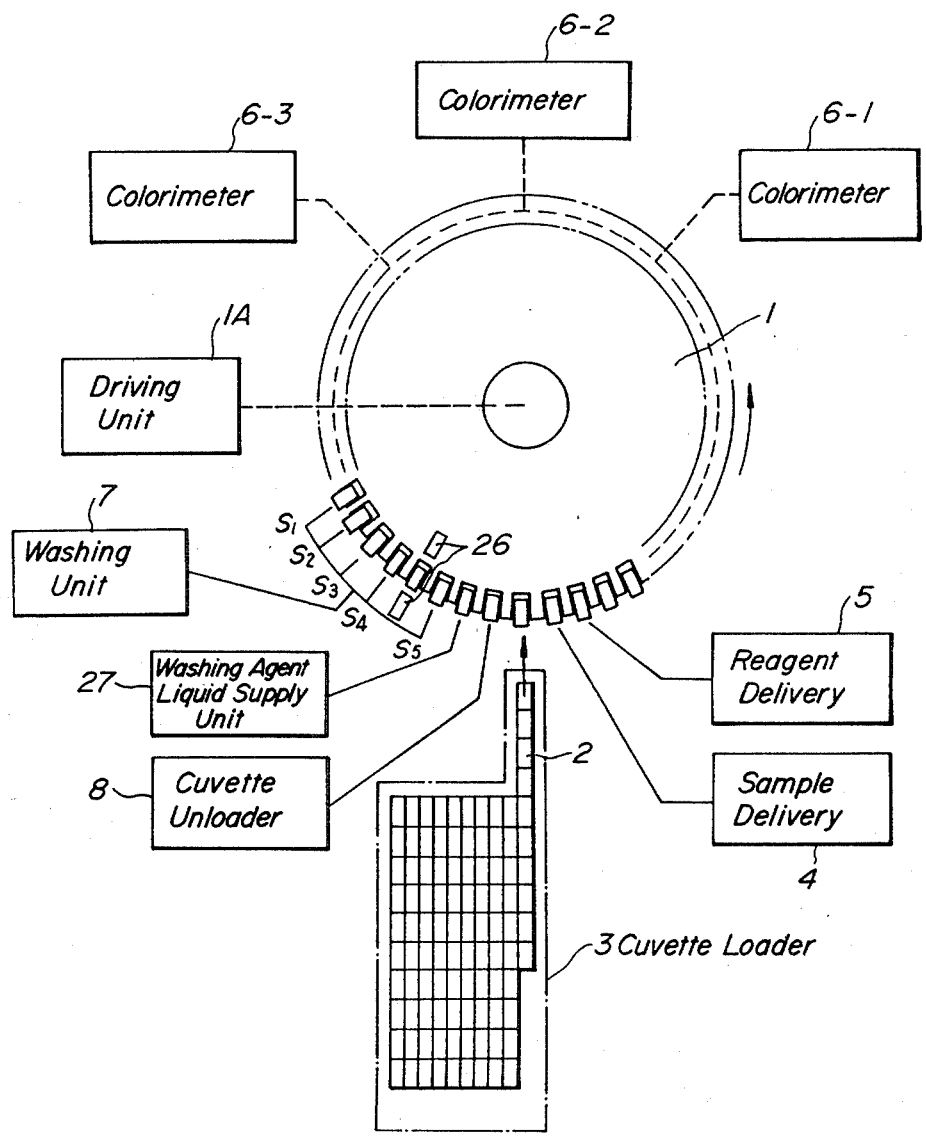
FIG_6

FIG_7
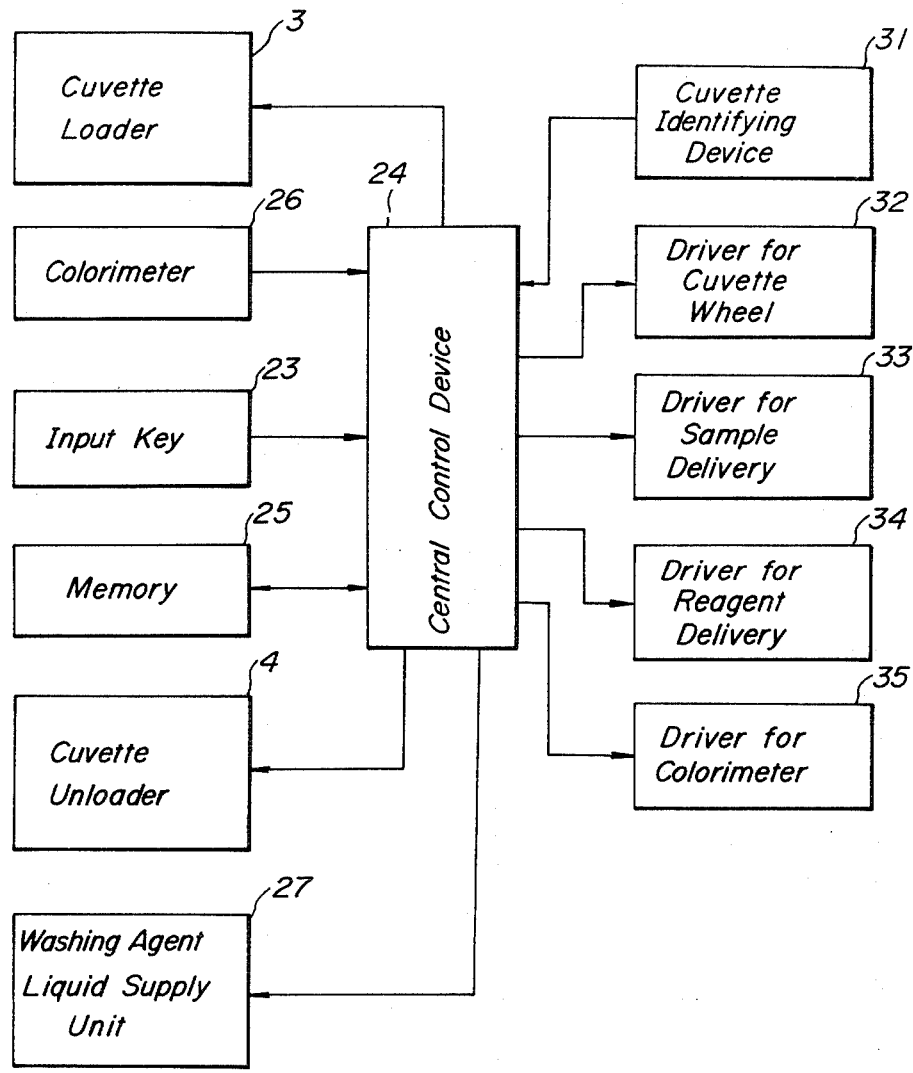

AUTOMATIC CHEMICAL ANALYZER WITH SELECTIVE REMOVAL OF REACTION VESSELS

BACKGROUND OF THE INVENTION

Field of the Invention and Related Art Statements

The present invention relates to an automatic chemical analyzer comprising an endless reaction line along which a plurality of reaction vessels are transported intermittently via a sample delivery position, a reagent delivery position and at least one photoelectrically measuring position.

Such an automatic chemical analyzer is disclosed in U.S. patent specification No. 4,406,547 issued on Sept. 27, 1983. In this known analyzer, each reaction vessel in the form of cuvette is not used repeatedly, but is discharged out of the reaction line after the measuremert using the relevant reaction vessel has been completed. To this end, the analyzer comprises an automatic cuvette loader for supplying reaction vessels successively onto a turntable and an automatic cuvette unloader for removing the reaction vessels from the turntable. Hereinbelow, this analyzer is termed a vessel wasting type.

There is further proposed another automatic chemical analyzer in which reaction vessels transported along an endless reaction line are repeatedly used. In this analyzer, after the measurement has been completed, the reaction vessel is washed to prepare a next measurement. Such an analyzer is called a vessel reusing type.

In the known analyzer of the vessel wasting type, a reaction vessel is wasted every time a single test has been done, so that the cost of the analysis is liable to be expensive.

In the known analyzer of the vessel reusing type, since reaction vessels are stained, damaged or deteriorated during repeated use, the reaction vessels have to be specially washed or exchanged periodically. Further, it is necessary to use new reaction vessels in accordance with test items or combinations thereof in view of contamination. In such a case, the reaction vessels have to be removed from the reaction line. However, in known analyzers of the vessel reusing type, the automatic cuvette loader and the automatic cuvette unloader are not provided, so that the cuvettes have to be exchanged manually. This operation is very cumbersome.

SUMMARY OF THE INVENTION

The present invention has for its object to provide a novel and useful automatic chemical analyzer which mitigates the above-mentioned drawbacks of the known automatic chemical analyzers by avoiding the cumbersome exchanging operation of cuvettes and by reducing the number of cuvettes to be wasted.

According to the invention, an automatic chemical analyzer comprises:

means for supporting and transporting a plurality of reaction vessels along an endless line;

means for automatically supplying reaction vessels to said supporting means;

means for delivering given amounts of samples to be analyzed into said reaction vessels;

means for delivering given amounts of reagents into said reaction vessels said samples and said reagents together forming test liquids;

means for measuring a property of said test liquids;

means for washing said reaction vessels;

means for removing said reaction vessels from said supporting means; and means for controlling the cuvette supplying means and cuvette removing means in accordance with a predetermined condition for exchanging reaction vessels such that reaction vessels are selectively removed from positions on the supporting means, after which new reaction vessels are supplied on the supporting means at said positions.

BRIEF DESCRIPTION OF THE DRAWINGS

FIG. 5 is a block diagram of the control unit of the analyzer illustrated in FIG. 4;

FIG. 6 is a schematic plan view showing a third embodiment of the automatic chemical analyzer according to the invention; and FIG. 7 is a block diagram of the control unit of the third embodiment.

DESCRIPTION OF THE PREFERRED EMBODIMENTS

Figure 1:
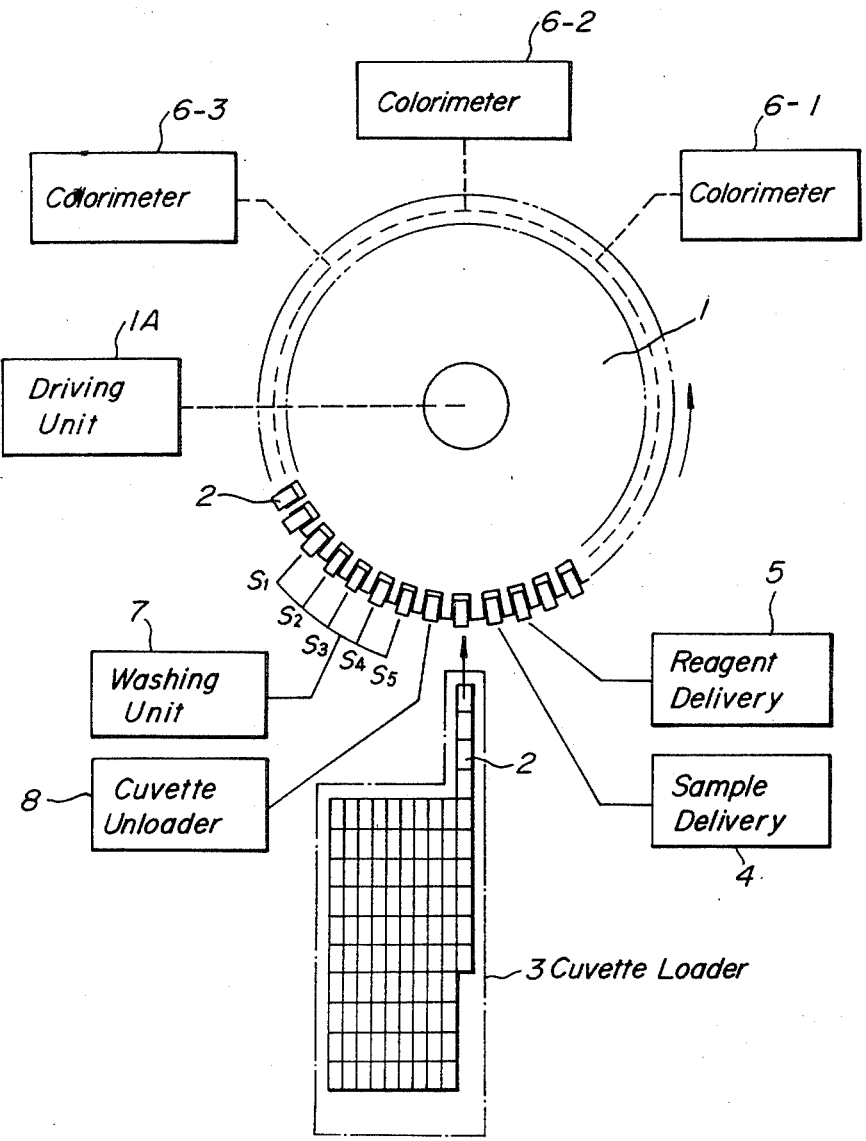
FIG. 1 is a schematic plan view showing a first embodiment of the automatic chemical analyzer according to the invention.

FIG. 1 is a schematic plan view showing a first embodiment of the automatic chemical analyzer according to the invention. The apparatus comprises a cuvette wheel 1 having a plurality of cuvette holding recesses formed equidistantly along a periphery of the cuvette wheel. The cuvette wheel 1 is rotated intermittently in a direction shown by an arrow by means of a suitable driving unit 1A. In each cuvette holding recess, respective cuvettes are removably fitted. Thus the cuvettes held in the cuvette holding recesses are transported along an endless circular reaction line in accordance with the rotation of the cuvette wheel 1.

Beside the cuvette wheel 1 are arranged an automatic cuvette loader 3, a sample delivery unit 4, a reagent delivery unit 5, a plurality of colorimetering units 6-1, 6-2, 6-3, washing unit 7 and an automatic cuvette unloader 8. Since the sample delivery unit, reagent delivery unit, colorimetering unit, washing unit, and cuvette unloader are well known in the relevant field of art, they are shown only schematically and their detailed explanation is omitted.

Now the general operation of the analyzer shown in FIG. 1 will be first explained. At first, the cuvette loader 3 supplies a cuvette 2 into a vacant cuvette holding recess formed in the periphery of the cuvette wheel 1. Then, the cuvette 2 is indexed at a sample delivery position and a given amount of a sample is delivered into the cuvette by means of the sample delivery unit 4. Next, the cuvette 2 is transferred into a reagent delivery position and a given amount of a reagent is poured into the cuvette. Since the analyzer can measure a plurality of test items, the reagent delivery unit 5 can deliver a given reagent specific to particular test item selected from a plurality of reagents. Then, in the cuvette 2 the sample and reagent are mixed with each other and the reaction proceeds to form a test liquid. After a given reaction time, an optical density of the reaction liquid contained in the cuvette 2 is measured by at least one of the colorimeters 6 1 to 6-3 by using light having a specific wavelength. After the measurement, the test liquid in the cuvette 2 is discharged and the cuvette is washed by the washing unit 7. If the relevant cuvette 2 can be repeatedly used for a next measurement, the cuvette is not removed by the cuvette unloader 8. Contrary to this, when the cuvette 2 is no longer usable for a next measurement, the cuvette is removed from the cuvette wheel 1 by the cuvette unloader 8. If a cuvette is removed from a cuvette holding recess of the cuvette wheel 1, a new cuvette holding is supplied into the relevant recess by means of the cuvette loader 3.

Figure 2:
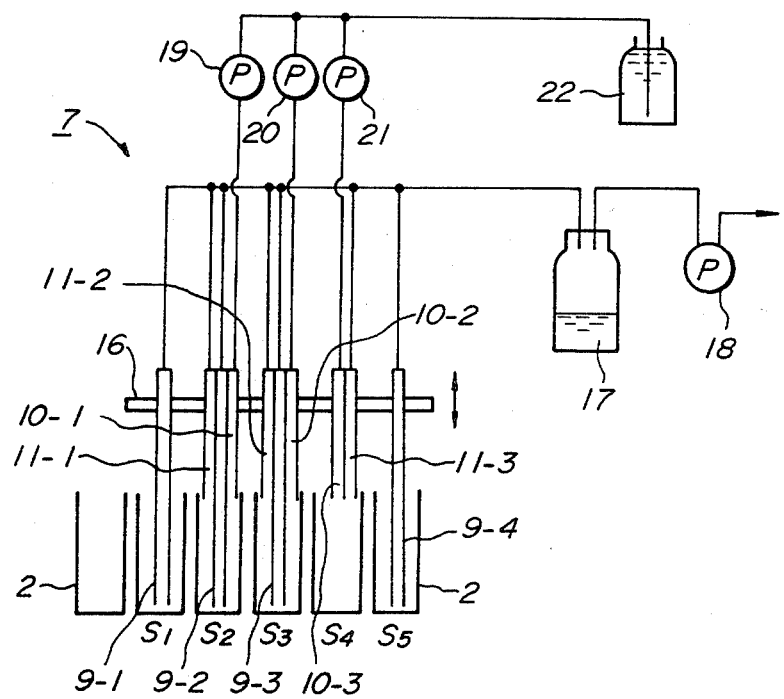
FIG. 2 is a schematic view illustrating a construction of a washing unit shown in FIG. 1.

FIG. 2 is a schematic view illustrating a detailed construction of the washing unit 7 shown in FIG. 1. A cuvette 2 containing a reaction liquid which has been analyzed is indexed into successive positions $S_1$ to $S_5$ in accordance with the intermittent rotation of the cuvette wheel 1. The washing unit 7 comprises liquid sucking nozzles 9-1, 9-2, 9-3 and 9-4 arranged at the positions $S_1$, $S_2$, $S_3$ and $S_5$, respectively, liquid supplying nozzles 10-1, 10-2 and 10-3 provided at the positions $S_2$, $S_3$ and $S_4$, respectively, and overflow nozzles 11-1, 11-2 and 11-3 arranged at the positions $S_2$, $S_3$ and $S_4$, respectively. These nozzles are secured to a holder 16 which is movable up and down as shown by a double-headed arrow in FIG. 2. The liquid sucking nozzles 9-1 to 9-4 and overflow nozzles 10-1 to 10-3 are connected to a vacuum pump 18 via a waste liquid bottle 17. The liquid supplying nozzles 10-1, 10-2 and 10-3 are coupled with a washing liquid tank 22 via liquid supply pumps 19, 20 and 21, respectively.

When a cuvette 2 containing a test liquid which has been analyzed is indexed at the position $S_1$, the reaction liquid is sucked by the nozzle 9-1. Next, at the position $S_2$, the washing liquid such as water is poured into the vacant cuvette 2 by means of the nozzle 10-1. After the cuvette is filled with the washing liquid, the overflow liquid is sucked by the nozzle 11-1. After the supply of the washing liquid from the nozzle 10-1 is stopped, the washing liquid remained in the cuvette is discharged by the nozzle 9-2. At the next position $S_3$, the same washing operation as that at the position $S_2$ is carried out by means of the nozzles 9-3, 10-2 and 11-2. In the position $S_4$, the cuvette 2 is filled with the washing liquid by means of the nozzles 10-3 and 11-3. In the last position $S_5$, the washing liquid contained in the cuvette 2 is sucked by the nozzle 9-4. In this manner, according to the present embodiment, the cuvette can be washed sufficiently, so that the cuvette can be used repeatedly for further analysis.

Figure 3:
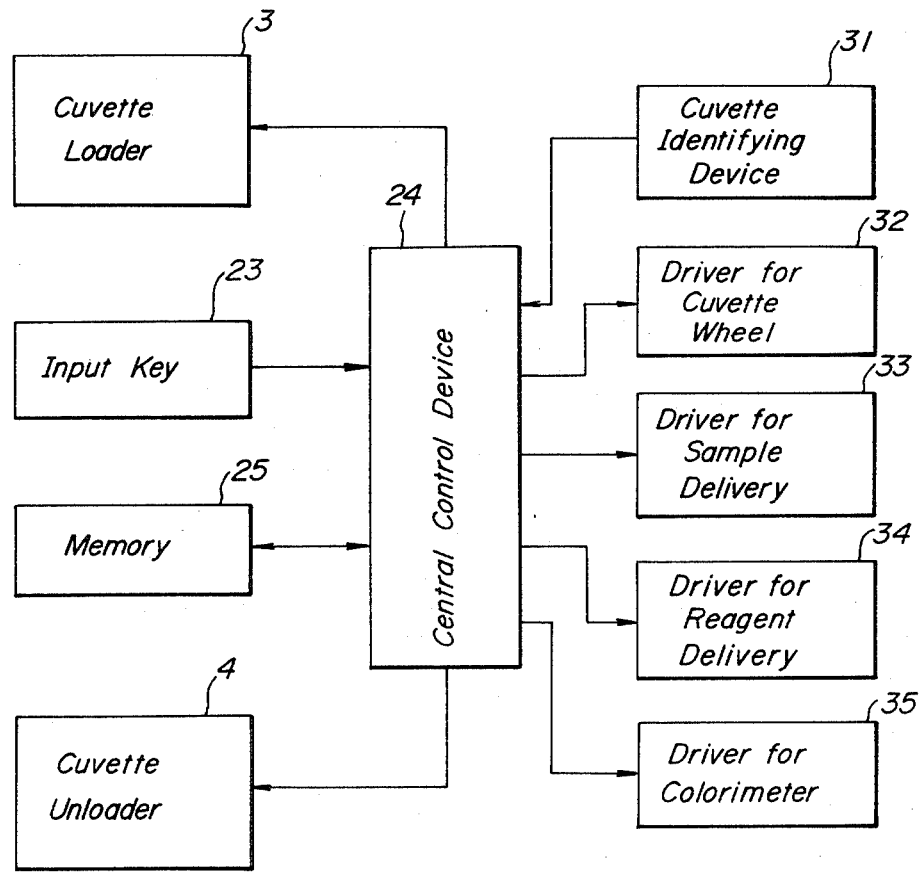
FIG. 3 is a block diagram depicting a control unit of the analyzer.

FIG. 3 is a block diagram showing a construction of a control unit of the present embodiment. The control unit comprises an input key 23 for entering necessary command or instruction for selectively exchanging cuvettes. The command thus entered as a cuvette exchange condition is stored in a memory 25 via a central control device 24. In the present embodiment, as the cuvette exchange condition the number of times (revolutions on the cuvette wheel 1) a single cuvette has been used repeatedly, and information as to test items to be analyzed are stored. The maximum number of repeated usages for which each of the cuvettes is to be employed may employed be set to any desired value using the input key 23. In analyses of ZTT (kunkel) and TTT (thymol), a cuvette cannot be used repeatedly due to possible contamination, so that once the measurement has been effected, the cuvette has to be discharged from the cuvette wheel and a new cuvette must be supplied from the cuvette loader. Further, when the analysis is to be conducted by using carriers on which antigen or antibody is fixed, a cuvette cannot be used repeatedly only by washing, so that the cuvette has to be removed from the cuvette wheel. Further, when the following test items are to be measured successively, the reaction vessel must be exchanged, TP (total protein)-Cu (copper); Alb (albumin)-TP; Alb-Fe; IgG (immunological globulin G)-Fe; IgA (immunological globulin A)-Fe; IgM (immunological globulin M)-Fe. For instance, after TP of a sample has been measured by using a certain vessel, when Cu is to be measured by using the relevant vessel, this vessel must be removed from the cuvette wheel 1 and a new vessel has to be supplied.

In the embodiment illustrated in FIG. 1, when a cuvette 2 has been repeatedly used the maximum number of times set using the input key 23, the cuvette is removed from the cuvette wheel 1 by means of the cuvette unloader 8 after the cuvette has been washed by the washing unit 7. Then a new cuvette is charged from the cuvette loader 3 into the cuvette holding recess of the cuvette wheel 1 from which the cuvette has just been removed. Moreover, immediately after a cuvette has been used to analyze a first test item of a specific combination entered by the input key 23, when the cuvette is to be used for the second test item of the relevant specific combination, that cuvette is removed from the cuvette wheel 1 whether or not the cuvette has been used the maximum number of times set using the input key 23. To this end, to the central control device 24 are connected cuvette identifying device 31, driver 32 for the cuvette wheel driving unit, driver 33 for the sample delivery device 4, driver 34 for the reagent delivery device 5, and driver 35 for the colorimeters 6-1, 6-2 and 6-3. In the present embodiment, since the washing unit 7 washes all cuvettes in regardless of whether the cuvette has been repeatedly used, it is not necessary to control the washing unit in accordance with the cuvette exchange condition.

Figure 4:
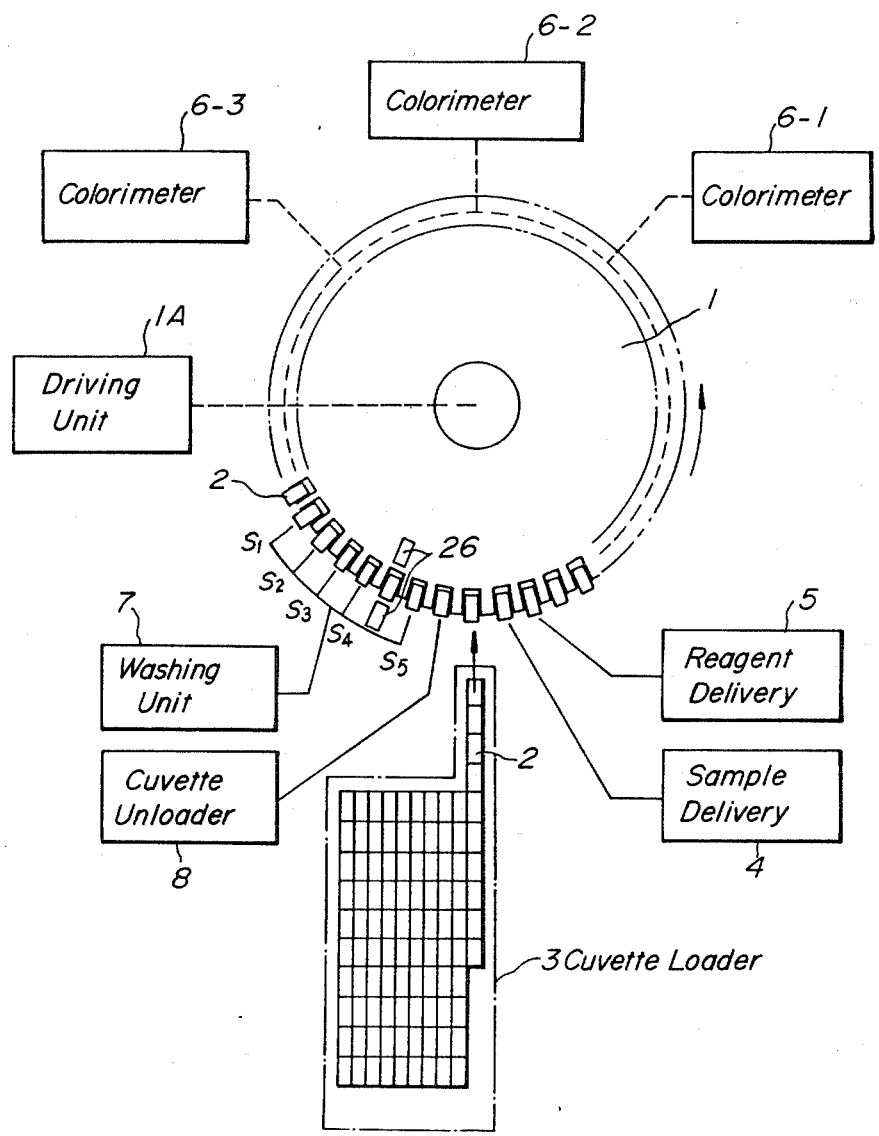
FIG. 4 is a schematic plan view illustrating a second embodiment of the automatic chemical analyzer according to the invention.

FIG. 4 is a schematic view showing a second embodiment of the automatic chemical analyzer according to the invention. In the present embodiment portions similar to those shown in FIG. 1 are denoted by the same reference numerals used in FIG. 1. This embodiment differs from the first embodiment in the point that a degree of deterioration, stain or dirtiness of one or more cuvette also may be set as a cuvette exchange condition. To this end, in the present embodiment, a colorimeter 26 is arranged between the positions $S_4$ and $S_5$ of the washing unit 7. Then the cuvette filled with the washing liquid is colorimetered by the colorimeter 26.

FIG. 5 is a block diagram showing a construction of the control unit of the embodiment shown in FIG. 4. An output signal of the colorimeter 26 is supplied to the control device 24 and is compared with a tolerable threshold level which has been previously stored in the memory 25 using the input key 23.

In this embodiment, when a detected level representing the dirtiness of a cuvette exceeds the threshold level, the relevant cuvette is discharged from the cuvette wheel 1 even though the cuvette has not yet been used the maximum number of times set using the input key 23. Therefore, the reliability of analysis using an analyzer in accordance with this embodiment is further enhanced. It should be noted that when a cuvette has been repeatedly used the maximum permissible number of times, the cuvette is removedfrom the cuvette wheel even if the detected level of dirtiness of the relevant cuvette does not exceed the threshold level. Further, when using a cuvette for a specific combination of test items, the cuvette is predominantly removed from the cuvette wheel.

FIG. 6 is a schematic plan view depicting a third embodiment of the automatic chemical analyzer according to the invention. Also in the present embodiment, portions similar to those shown in FIG. 4 are represetned by the same reference numerals used in FIG. 6. In this embodiment, a washing agent liquid supply unit 27 is provided between the washing unit 7 and the cuvette unloader 8.

When a detected dirtiness level of a cuvette is larger than the threshold level, a washing agent liquid is poured into the cuvette by the supplying unit 27 controlled by the control device 24 as shown in FIG. 7. Then the relevant cuvette is not used, and is transported again into the washing unit 7. In the washing unit 7, the cuvette is washed again and is filled with the washing liquid. Then the cuvette is measured by the colorimeter 26 to again detect a level of dirtiness. This dirtiness level is compared with the threshold level. If the detected level is still higher than the threshold level, after the washing liquid has been sucked by the nozzle 9-4 at the position $S_5$ of the washing unit 7, the cuvette is removed from the cuvette wheel 1 by means of the cuvette unloader 8. In this case, the washing agent liquid supplying unit 27 is not operated. If the detected level is lower than the threshold level, the cuvette is further used until the maximum number of times is reached, while the dirtiness is monitored.

The present invention is not limited to the embodiments so far explained, but many modifications within the spirit of the present invention can be perceived by those skilled in the art.

For instance, in the second and third embodiments the output signal of the colorimeter 26 can be adopted as a sole cuvette exchange condition. Further, in the third embodiment, the function of the washing agent liquid supplying unit 27 may be incorporated in the washing unit 7. Moreover, in the first embodiment shown in FIG. 1, the cuvette unloader 8 may be arranged at an upstream position to the washing unit 7. Further, a plurality of washing agent liquids may be prepared and an effective washing agent liquid may be selectively supplied to a cuvette in accordance with a test item. Moreover, as the cuvette exchange condition, a detected concentration of substance contained in a sample may be used. In such a case, when an abnormally high concentration is detected, a cuvette used in the relevant measurement may be exchanged by a new one. Such a cuvette exchange condition is particularly effective in immunological analysis.

As explained above in detail, according to the invention, since a cuvette is not always wasted after a single measurement has been completed, the running cost of analysis can be reduced. Moreover, cuvettes are automatically exchanged in accordance with the cuvette exchange condition, and the operator is completely free from the cuvette exchange operation. Further, the possible contamination can be effectively avoided by exchanging cuvettes, so that the accuracy of analysis can be improved. In this manner, the automatic chemical analyzer according to the invention can be utilized in a wide range of analyses, from biochemical analysis to immunological analysis.

What is claimed is:

1. An automatic chemical analyzer comprising
means for supporting and transporting a plurality of reaction vessels along an endless line;
means for automatically supplying reaction vessels to said supporting means;
means for delivering given amounts of samples to be analyzed into said reaction vessels;
means for delivering given amounts of reagents into said reaction vessels, said samples and said reagents together forming test liquids;
means for measuring a property of said test liquids;
means for washing said reaction vessels;
means for removing said reaction vessels from said supporting means; and
means for controlling the reaction vessel supplying means and reaction vessel removing means, said controlling means comprising a means for detecting a degree of dirtiness for each of said reaction vessels, such that said reaction vessels are selectively removed from positions on the supporting means when the detected degrees of dirtiness of the reaction vessels exceed a threshold level, after which reaction vessels are supplied to said positions on the supporting means by said supplying means.

2. An analyzer according to claim 1, wherein said controlling means further comprises an input key for entering commands relating to said degree of dirtiness, a memory for storing the commands entered by the input key and a control device connected to said input key and memory for producing control signals to be supplied to the reaction vessel supplying means and the reaction vessel removing means.

3. An analyzer according to claim 1, wherein said colorimeter is arranged in the washing means, so that the degree of dirtiness of each of said reaction vessels is detected while said each reaction vessel is filled with a washing liquid.

4. An analyzer according to claim 1, wherein said controlling means further comprises means for supplying a washing agent liquid into a reaction vessel when the degree of dirtiness of that reaction vessel as detected by said colorimeter exceeds said threshold level.

* * * * *